(12) United States Patent
Chitre et al.

(10) Patent No.: US 8,808,769 B2
(45) Date of Patent: Aug. 19, 2014

(54) METHOD FOR EXTRACTION OF FRACTIONS CONTAINING PHARMACOLOGICALLY ACTIVE INGREDIENTS WITH LESS CYTOTOXICITY FROM ONE OR MORE PLANTS

(75) Inventors: Deepa Chitre, Los Gatos, CA (US); Debendranath Dey, Fremont, CA (US)

(73) Assignee: Bioved Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 13/322,147

(22) PCT Filed: May 21, 2010

(86) PCT No.: PCT/IN2010/000350
§ 371 (c)(1),
(2), (4) Date: Nov. 22, 2011

(87) PCT Pub. No.: WO2010/134100
PCT Pub. Date: Nov. 25, 2010

(65) Prior Publication Data
US 2012/0070519 A1    Mar. 22, 2012

(30) Foreign Application Priority Data

May 22, 2009  (IN) .......................... 1284/MUM/2009

(51) Int. Cl.
*A61K 36/906*    (2006.01)
(52) U.S. Cl.
USPC ........................................................ 424/756
(58) Field of Classification Search
None
See application file for complete search history.

(56) References Cited

FOREIGN PATENT DOCUMENTS

JP          10120510 A   *   5/1998
WO      WO 0145701 A1   *   6/2001

OTHER PUBLICATIONS

"Tutorial 3.5-Solvent Extraction". Internet Archive Date: Jul. 6, 2011 [Retrieved from the Internet on: Mar. 9, 2013]. Retrieved from: <URL: http://web.archive.org/liveweb/http://www.epa.gov/safewater/radionuclides/training/transcripts/tutorial_3.5.pdf>.*
"Veda Living". Internet Date: 2009 [Retrieved from the Internet on: Mar. 6, 2013]. Retrieved from the Internet: <URL: http://www.vedaliving.com/factor-extraction-process.php>.*
"American Chemical Society". Internet Date: Jan. 25, 2013 [Retrieved from the Internet on: Mar. 6, 2013]. Retrieved from the Internet: <URL: http://www.cancer.org/treatment/understandingyourdiagnosis/talkingaboutcancer/whensomeoneyouknowhascancer/when-somebody-you-know-has-cancer-cancer-treatment-questions>.*

* cited by examiner

*Primary Examiner* — Amy L Clark
(74) *Attorney, Agent, or Firm* — Timberline Patent Law Group PLLC (57) ABSTRACT

A method of obtaining one or more fractions from one or more plants is disclosed. The method includes subjecting one or more parts of the one or more plants to hydro-alcoholic extraction in presence of a water-insoluble solvent to obtain one or more extracts. The method further includes subjecting the one or more extracts to one or more of de-pigmentation, de-fatting and detoxification process to obtain the one or more fractions. The one or more fractions thus obtained contain a desired pharmacologically active ingredient in concentration greater than concentrations of other pharmacologically active ingredients present in the at least one fraction. Further, the one or more fractions are less toxic as compared with corresponding one or more fractions obtained by conventional methods. In addition, the one or more fractions are therapeutically more effective in various diseases as compared to one or more fractions obtained by conventional methods.

3 Claims, 5 Drawing Sheets

| Method 1 | | Method 2 | | Rf |
|---|---|---|---|---|
| Visualization At 254 nm | After Derivatization At 580 nm | Visualization At 254 nm | After Derivatization At 580 nm | |
| | 9864.3 | | 27307.4 | 0.08 |
| | 7940.9 | 8967.3 | | 0.14 |
| 13412.9 | 4647.2 | 35743.8 | 16720.2 | 0.22 |
| 2851.3 | | 7551.4 | | 0.26 |
| 3041.2 | 7752.5 | 4580 | 28048.9 | 0.33 |
| 6273 | | 6598.2 | 14083.2 | 0.42 Neo-andrographolide |
| | 3119.8 | | | 0.48 |
| | | 7359.2 | | 0.51 |
| | 3141.7 | | 10008.9 | 0.61 Andrographolide |
| | 2207.4 | | 3735.6 | 0.7 14-deoxy-11,12 didehydroandrographolide |

FIG. 1

| Ocimum Sanctum (15ml) | | | | |
|---|---|---|---|---|
| Method 1 | | Method 2 | | Rf |
| Visualization | After Derivatization | Visualization | After Derivatization | |
| At 254 nm | At 580 nm | At 254 nm | At 580 nm | |
| 6058.9 | 17599 | 4787.1 | 30501.2 | 0.16 DL-linalool |
| 3668.3 | 10049 | 2068.8 | 15556 | 0.21 |
| 5799.1 | | 1866.5 | | 0.26 |
| | | 2454.9 | 16643.7 | 0.29 |
| 5821.3 | 10568.8 | 4923.7 | 9715.8 | 0.32 Eucalyptol |
| | 6083.2 | | | 0.47 |
| | 2297.4 | | 3123.4 | 0.54 |
| | 9584.1 | | 26495 | 0.72 Euganol |

FIG. 2

| Solanum Xanthocarpum (15ml) | | | | |
|---|---|---|---|---|
| Method 1 | | Method 2 | | Rf |
| Visualization | After Derivatization | Visualization | After Derivatization | |
| At 254 nm | At 580 nm | At 254 nm | At 580 nm | |
|  | 11765.2 | 3207.3 |  | 0.11 |
|  | 4426.7 |  | 15114 | 0.18 |
| 2568.8 | 9269 | 13570.6 | 17200 | 0.22 Solasonine (Tentative) |
|  |  | 2791.5 | 12657.4 | 0.29 Solasodine (Tentative) |
|  |  | 1301.8 |  | 0.31 |
|  |  | 3903.7 | 14014.8 | 0.34 Solamargine (Tentative) |
|  |  | 3247.8 |  | 0.54 |
|  | 4562.6 | 3157.2 |  | 0.59 |
|  | 15457.4 |  | 68402.6 | 0.67 |

METHOD FOR EXTRACTION OF FRACTIONS CONTAINING PHARMACOLOGICALLY ACTIVE INGREDIENTS WITH LESS CYTOTOXICITY FROM ONE OR MORE PLANTS

FIELD OF THE INVENTION

The invention generally relates to method of extracting one or more fractions from one or more plants. More specifically, the invention relates to methods of extracting one or more pharmacologically active fractions including a desired pharmacologically active ingredient in a predominant concentration as compared to concentrations of other pharmacologically active ingredients present in the one or more fractions.

BACKGROUND OF THE INVENTION

The medicinal uses of natural products obtained from various plants are well known for a long time now. The medicinal uses of these natural products offer several benefits. For example, these natural products do not cause any relevant side effects. Therefore, in order to exploit the medicinal applicability of these natural products, efforts have been made to extract different pharmacologically active ingredients from various plants. Accordingly, several methods of extraction of pharmacologically active ingredients from various plants exist in the art.

Pharmacologically active ingredients are secondary metabolites of a plant that are usually present deep inside the tissues of the plant. Usually, production of the secondary metabolites in a plant is often very low. Generally, pharmacologically active ingredients of a plant constitute less than 1% of the total weight of the plant (weight taken as a dry plant). In addition, the percentage of pharmacologically active ingredients in a plant depends on physiological and developmental stage of the plant. For example, an immature plant yields lesser percentage of pharmacologically active ingredients as compared to a matured plant. Further, since the secondary metabolites exist deep inside the tissues of a plant, penetration of an extraction solvent deep into the tissues of the plant becomes important. Therefore, these critical factors need to be considered for developing extraction processes for obtaining fractions containing optimum quantities of pharmacologically active ingredients.

The existing methods for extracting pharmacologically active ingredients from various plants yield fractions containing desired pharmacologically active ingredients along with undesired pharmacologically active ingredients in a sufficient amount to cause cytotoxicity. In addition, the fractions containing desired pharmacologically active ingredients may contain a certain amount of pigments and lipids, which may render cytotoxicity to the fractions containing desired pharmacologically active ingredients either directly or indirectly by co-association with other cytotoxic agents.

Therefore, there is a need in the art for a method of extracting fractions containing desired pharmacologically active ingredients, wherein the fractions are less cytotoxicity and are therapeutically more effective in various diseases as compared to corresponding fractions obtained using conventional methods.

BRIEF DESCRIPTION OF FIGURES

The accompanying figures, incorporated in and form part of the specification, serve to illustrate various examples in accordance with the present invention.

DETAILED DESCRIPTION OF THE INVENTION

Before describing in detail embodiments that are in accordance with the invention, it should be observed that the embodiments reside primarily in combinations of method steps related to extraction of one or more fractions from one or more plants and the one or more fractions. Accordingly, the method steps and the one or more fractions have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process and method that comprises a list of method steps does not include only those method steps but may include other method steps not expressly listed or inherent to such process and method.

Generally speaking, pursuant to the various embodiments, the invention provides a method of extracting one or more pharmacologically active fractions from one or more plants. The one or more fractions include a desired pharmacologically active ingredient in a predominant concentration as compared to concentrations of other pharmacologically active ingredients present in the one or more fractions.

In accordance with various embodiments, the method includes extracting one or more fractions from one or more plants. The one or more plants may be, for example, but are not limited to, *Andrographis paniculata, Solanum xanthocarpum, Trigonella foenum graecum, Curcuma longa, Zingiber officinalis, Boswellia serrata, Bacopa monieri, Picrorrihza kurroa*, and *Ocimum sanctum*. The method may be used to extract one or more fractions from various plants in addition to the one or more plants disclosed herein.

It should be understood that the invention resides in the method of extracting one or more fractions from one or more plants. Accordingly, the method, as disclosed herein, may be applied to any plant, that may or may not be disclosed herein, for extraction of one or more fractions therefrom, without departing from the scope of the invention.

The method includes obtaining a plant material from the one or more plants. The plant material may include, for example, but not limited to, one or more fresh parts of the one or more plants and one or more dried parts of the one or more plants. The plant material may also be one or more of, but are not limited to, one or more whole plant, leaves, roots, bark, stems, flowers, fruits, exudates, and any other part of the one or more plant containing one or more pharmacologically active ingredients.

The plant material may be processed chemically or physically before initiating the method. Physical processing of the plant material may include, for example, but not limited to, size reduction. Whereas, chemical processing of the plant material may include, for example, but not limited to, treating the plant material with one or more chemicals, washing with water, and the like. Optionally, an un-processed plant material may also be used in the method. For example, the plant material may be coarse powder of dried leaves of *Andrographis paniculata*. Alternatively, the plant material may be coarse powder of dried fruits of *Solanum xanthocarpum*.

The plant material thus obtained from the one or more plants is then subjected to hydro-alcoholic extraction in presence of a water-insoluble solvent. The hydro-alcoholic extraction includes soaking the plant material in a mixture of aqueous alcohol and the water-insoluble solvent for a predetermined time. The water-insoluble solvent used in the hydro-alcoholic extraction may be one of, but not limited to, chloroform, acetone, dichloromethane and tetra-chloromethane. Any other similar water-insoluble solvent may be used in the hydro-alcoholic extraction without departing from the scope of the invention.

An alcohol present in the aqueous alcohol may be, for example, but is not limited to, methanol, ethanol, propanol, amyl alcohol, isopropyl alcohol and any other alcohol with a polarity similar to polarity of the alcohol. Alternatively, any alcohol with a dipole movement comparable with one or more of methanol, ethanol, propanol, amyl alcohol and isopropyl alcohol may be used without departing from the scope of the invention. For example, the alcohol present in the aqueous alcohol may be methanol.

Further, the concentration of the alcohol in the aqueous alcohol may range from 6% v/v to 95% v/v. The concentration of alcohol may be selected based on the plant material used in the method. For example, when the plant material is a fresh plant material, the concentration of the alcohol in the aqueous alcohol may range from 6% v/v to 90% v/v. Whereas, when the plant material is a dry plant material, concentration of the alcohol in the aqueous alcohol may range from 20% v/v to 86% v/v. More preferably, the concentration of the alcohol in the aqueous alcohol may range from 40% v/v to 80% v/v irrespective of whether the plant material is the dry plant material or the fresh plant material. However, the concentration of the alcohol in the aqueous alcohol may be varied based on the plant material used in the method without departing from the scope of the invention.

The water-insoluble solvent and the aqueous alcohol together form a mixture for hydro-alcoholic extraction of the plant material. In other words, the plant material is subjected to hydro-alcoholic extraction with the mixture of the water-insoluble solvent and the aqueous alcohol. The hydro-alcoholic extraction includes soaking the plant material in the mixture of the aqueous alcohol and the water-insoluble solvent for a predetermined time. In an embodiment, the predetermined time may range from 6 hours to 48 hours. In another embodiment, the plant material may be soaked in the mixture of the aqueous alcohol and the water-insoluble solvent overnight (8 hours to 12 hours). The predetermined time of soaking the plant material may range from few hours to several days depending upon the conditions and objectives of the hydro-alcoholic extraction without departing from the scope of the invention.

The mixture may be occasionally stirred while the mixture is allowed to soak. The stirring may be accomplished using methods known in the art. For example, the stirring may be achieved by using any appropriate laboratory or industrial stirrer/shaker or optionally the mixture may be stirred manually by using an appropriate stirrer, for example, a rod.

Soaking of the plant material in the mixture for the predetermined time constitutes maceration. Generally, the secondary metabolites that constitute the pharmacologically active ingredients in the plant material are located deep inside the tissues of the plant material. Therefore, in order to extract the pharmacologically active ingredients effectively, the water-insoluble solvent and the aqueous alcohol present in the mixture should penetrate the tissues and/or cells of the plant material. The secondary metabolites may then dissolve in the solvent and may be further extracted.

Water present in the aqueous alcohol swells the tissues of the plant material and dissolves one or more pharmacologically active ingredients of the one or more plants. Further, the alcohol being a more potent extraction solvent with a wide range of solubility dissolves additional pharmacologically active ingredients present in the one or more plants. The use of water-insoluble solvent helps in extraction of other pharmacologically active ingredients of the one or more plants in addition to the pharmacologically active ingredients extracted by the alcohol and water. Thus, soaking of the plant material in the mixture of the aqueous alcohol and the water-insoluble solvent results in extraction of the pharmacologically active ingredients of the one or more plants in two different phases. The two different phases may be a hydro-alcoholic phase and a water-insoluble phase.

After the predetermined time is over, the mixture is filtered. The filtration may be carried out using the methods generally known and used in the art of liquid-liquid extraction. Alternatively, the filtration may be achieved by using appropriate laboratory or industrial filtration procedures. As a result of filtering the mixture, a first residue and a first filtrate is obtained.

The first residue obtained as a result of filtering the mixture is kept aside and used later for re-extraction. Whereas, the first filtrate obtained as a result of filtering the mixture is allowed to settle. The first filtrate includes two immiscible layers. The two immiscible layers include a first aqueous layer and a first non-aqueous layer. The first aqueous layer and the first non-aqueous layer become visually distinct when the mixture is allowed to settle. The first aqueous layer and the first non-aqueous layer thus visually distinguished are then separated using one or more methods known in the art. For example, the first aqueous layer and the first non-aqueous layer may be separated using a separating funnel when the method is carried out on a laboratory scale. Whereas, the first aqueous layer and the first non-aqueous layer may be separated using appropriate solvent partitioning techniques known in the art of liquid-liquid extraction when the method is carried out on an industrial scale.

The first aqueous layer and the first non-aqueous layer thus separated are then separately subjected to a step of concentrating the first aqueous layer and the first non-aqueous layer to obtain a first dry extract and a second dry extract respectively. The step of concentrating the first aqueous layer and the first non-aqueous layer may include, one or more of, but are not limited to, drying, evaporating and vacuum evaporating the first aqueous layer and the first non-aqueous layer, separately.

For example, the first aqueous layer is subjected to evaporation using the methods known in the art. The evaporation may be carried out until the time the water and the alcohol in the first aqueous layer are completely evaporated to obtain the first dry extract. The first dry extract thus obtained constitutes a first hydro-alcoholic fraction. Whereas, the first non-aqueous layer is subjected to evaporation using the methods known in the art. The evaporation may be carried out until the time the water-insoluble solvent in the first non-aqueous layer is completely evaporated to obtain the second dry extract. The second dry extract thus obtained constitutes a first non-aqueous fraction. The first dry extract and the second dry extract are then weighed separately. The first dry extract is kept aside and the second dry extract is used for subsequent steps of the method.

The second dry extract is then subjected to one or more of a de-pigmentation process, a de-fatting process, and a detoxification process. The one or more of the de-pigmentation process, the de-fatting process, and the detoxification process may include treating or dissolving the second dry extract in one or more of a de-pigmenting agent, a de-fatting agent, and a detoxifying agent. For example, the second dry extract may be dissolved in the one or more of the de-pigmenting agent, the de-fatting agent, and the detoxifying agent. Use of the one or more of the de-pigmenting agent, the de-fatting agent, and the detoxifying agent as solvents in the method facilitates removal of one or more of lipids, pigments and toxins from the plant material that otherwise may impart toxicity to the one or more fractions obtained from the plant material.

The one or more of the de-pigmenting agent, the de-fatting agent, and the detoxifying agent may be a single organic solvent having one or more properties of de-pigmenting, de-fatting and detoxifying the second dry extract. Alternatively, the de-pigmenting agent, the de-fatting agent, and the detoxifying agent may include two or more agents having one or more properties of de-pigmenting, de-fatting and detoxifying the second dry extract. The one or more of the de-pigmenting agent, the de-fatting agent, and the detoxifying agent may be selected from the group consisting of pentane, hexane, heptanes, diethyl ether, petroleum ether, ethylene chloride, methylene chloride, cyclohexane, solvent ether and the like. In an exemplary embodiment, the process of de-pigmentation, de-fatting and detoxification includes dissolving the second dry extract in hexane.

Dissolution of the second dry extract yields a first solution. The first solution is then filtered to obtain a second residue and a second filtrate. The second filtrate thus obtained is discarded. Whereas the second residue obtained as a result of filtering the first solution is dried and weighed. The second residue constitutes a first fraction of the one or more fractions. The first fraction contains the desired pharmacologically active ingredient in a concentration predominantly greater than concentrations of other pharmacologically active ingredients present in the first fraction.

Thereafter, the first residue obtained as a result of filtering the mixture and that is kept aside, earlier, is subjected to a re-extraction process. The re-extraction process includes subjecting the first residue to hydro-alcoholic extraction in presence of the water-insoluble solvent. The hydro-alcoholic extraction includes soaking the first residue in the mixture of aqueous alcohol and the water-insoluble solvent for a particular time. In an embodiment, the particular time may range from 6 hours to 48 hours. The mixture may be occasionally stirred while the mixture is allowed to soak. After the particular time is over, the mixture is filtered to obtain a third residue and a third filtrate.

The third filtrate thus obtained includes two immiscible layers. The two immiscible layers include a second aqueous layer and a second non-aqueous layer. The second aqueous layer and the second non-aqueous layer are then separated and concentrated separately to obtain a third dry extract and a fourth dry extract respectively. The fourth dry extract thus obtained constitutes a second non-aqueous fraction. The third dry extract and the fourth dry extract are then weighed separately. The third dry extract is kept aside and the fourth dry extract is used for subsequent steps of the re-extraction process.

Subsequently, the fourth dry extract is dissolved in the one or more of the de-pigmenting agent, the de-fatting agent, and the detoxifying agent. Dissolution of the fourth dry extract yields a second solution. The second solution is then filtered to obtain a fourth residue and a fourth filtrate. The fourth residue thus obtained constitutes a second fraction of the one or more fractions. The second fraction contains the desired pharmacologically active ingredient in a concentration predominantly greater than concentrations of other pharmacologically active ingredients present in the second fraction.

A total yield of the one or more fractions is calculated as sum of yields of the first fraction and the second fraction. The one or more fractions thus obtained contain the desired pharmacologically active ingredient in a concentration predominantly greater than the concentrations of other pharmacologically active ingredients present in the one or more fractions.

In an exemplary embodiment, a plant is *Andrographis paniculata* and the desired pharmacologically active ingredient is andrographolide. The one or more fractions obtained from *Andrographis paniculata* in accordance with the various embodiments of the invention contain andrographolide in a predominant concentration as compared to concentrations of other pharmacologically active ingredients present in the one or more fractions. The method includes extracting one or more fractions from powder of dried leaves of *Andrographis paniculata* (the plant material). The powder of the dried leaves of *Andrographis paniculata* is soaked in a mixture of 60% methanol and chloroform overnight (about 8 hours to 12 hours). Thereafter, the mixture is filtered to obtain a first residue and a first filtrate. The first residue is kept aside for subsequent use in a re-extraction process and the first filtrate is allowed to settle. The first filtrate that is allowed to settle includes two immiscible layers. The two immiscible layers include a methanol layer and a chloroform layer. The methanol layer and the chloroform layer are separated using a separating funnel. Subsequently the methanol layer and the chloroform layer are separately subjected to evaporation to obtain a first dry aqueous methanolic extract and a first dry chloroform extract.

The first dry chloroform extract is then dissolved in hexane to obtain a first solution. Dissolution of the first dry chloroform extract in hexane allows one or more of de-fatting, de-pigmenting and detoxification of the powder of the dried leaves of *Andrographis paniculata* that is being extracted. The first solution is then filtered to obtain a second residue and a second filtrate. The second residue thus obtained constitutes a first fraction of the one or more fraction containing andrographolide in a concentration greater than concentrations of other pharmacologically active ingredients present in the first fraction.

Thereafter, the first residue, obtained earlier, is subjected to the re-extraction process. The re-extraction process includes soaking the first residue in a fresh mixture of 60% methanol and chloroform overnight (about 8 hours to 12 hours). The mixture is then filtered to obtain a third residue and a third filtrate. The third residue may either be discarded or subjected to further re-extraction. Whereas, the third filtrate is allowed to settle. The third filtrate includes two immiscible layers. The two immiscible layers include a methanol layer and a chloroform layer. The methanol layer and the chloroform layer are separated using a separating funnel. Subsequently the methanol layer and the chloroform layer are separately subjected to evaporation to obtain a second dry aqueous methanolic extract and a second dry chloroform extract.

The second dry aqueous methanolic extract constitutes a second aqueous methanolic fraction. Whereas, the second dry chloroform extract is further dissolved in hexane to obtain a second solution. The second solution is then filtered to obtain a fourth residue and the fourth filtrate. The fourth filtrate is discarded and the fourth residue is dried and weighed separately. The fourth residue thus obtained constitutes a second fraction of the one or more fractions. The second fraction thus obtained contains andrographolide in a concentration predominantly greater than concentrations of other pharmacologically active ingredients present in the second fraction. Total yield of the one or more fractions may be calculated as sum of yields of the first fraction and the second fraction.

In another exemplary embodiment, the one or more fractions obtained from *Solanum xanthocarpum* in accordance with the various embodiments of the invention contain solasodine in a predominant concentration as compared to concentrations of other pharmacologically active ingredients present in the one or more fractions. The method includes extracting one or more fractions from powder of dried fruits of *Solanum xanthocarpum* (the plant material). The powder of the dried fruits of *Solanum xanthocarpum* is soaked in a mixture of 60% methanol and chloroform overnight (about 8 hours to 12 hours). Thereafter, the mixture is filtered to obtain a first residue and a first filtrate. The first residue is kept aside for subsequent use in a re-extraction process and the first filtrate is allowed to settle. The first filtrate includes two immiscible layers. The two immiscible layers include a methanol layer and a chloroform layer. The methanol layer and the chloroform layer are separated using a separating funnel. Subsequently the methanol layer and the chloroform layer are separately subjected to evaporation to obtain a first dry aqueous methanolic extract and a first dry chloroform extract.

The first dry chloroform extract is then dissolved in hexane to obtain a first solution. Dissolution of the first dry chloroform extract in hexane allows one or more of de-fatting, de-pigmenting and detoxification of the powder of the dried leaves of *Solanum xanthocarpum* that is being extracted. The first solution is then filtered to obtain a second residue and a second filtrate. The second residue thus obtained constitutes a first fraction of the one or more fraction containing solasodine in a concentration greater than concentrations of other pharmacologically active ingredients present in the first fraction.

Thereafter, the first residue, obtained earlier, is subjected to the re-extraction process. The re-extraction process includes soaking the first residue in a fresh mixture of 60% methanol and chloroform overnight (about 8 hours to 12 hours). The mixture is then filtered to obtain a third residue and a third filtrate. The third residue may either be discarded or subjected to further re-extraction and the third filtrate is allowed to settle. The third filtrate includes two immiscible layers. The two immiscible layers include a methanol layer and a chloroform layer. The methanol layer and the chloroform layer are separated using a separating funnel. Subsequently the methanol layer and the chloroform layer are separately subjected to evaporation to obtain a second dry aqueous methanolic extract and a second dry chloroform extract.

The second dry aqueous methanolic extract constitutes a second aqueous methanolic fraction. Whereas, the second dry chloroform extract is further dissolved in hexane to obtain a second solution. The second solution is then filtered to obtain a fourth residue and the fourth filtrate. The fourth filtrate is discarded whereas the fourth residue is dried and weighed separately. The fourth residue thus obtained constitutes a second fraction of the one or more fractions. The second fraction thus obtained contains solasodine in a concentration predominantly greater than concentrations of other pharmacologically active ingredients present in the second fraction. Total yield of the one or more fractions may be calculated as the sum of yields of the first fraction and the second fraction.

The one or more fractions obtained in accordance with various embodiments of the invention contain a desired pharmacologically active ingredient in concentration predominantly greater than concentrations of other pharmacologically active ingredients present in the one or more fractions. Further, the one or more fractions are less toxic as compared with corresponding one or more fractions obtained by conventional methods. In addition, the one or more fractions are therapeutically more effective in various diseases as compared to one or more fractions obtained by conventional methods.

As illustrated in the examples below and the various embodiments above, the method may be used to extract one or more fractions containing a desired pharmacologically active ingredient in a predominantly greater concentration as compared with one or more fractions obtained using conventional methods of extraction. For example, when the method of invention is applied to *Solanum xanthocarpum*, a fraction containing a predominant concentration of solasodine as compared to other pharmacologically active ingredients present in the fraction. Similarly, when the method is applied to any other plant to obtain one or more fractions, the one or more fractions thus obtained may contain a particular pharmacologically active ingredient in a predominant concentration.

Further, the one or more fractions thus obtained are therapeutically effective in one or more diseases. Depending upon the medicinal use of the plant material used in the method, the one or more fractions obtained from the plant material may be effective in corresponding diseases. For example, the one or more fractions obtained from *Andrographis paniculata* that predominantly contain andrographolide are effective in one or more of, but are not limited to, inhibiting growth of one or more micro-organism in mammals, inhibiting one or more pro-inflammatory cytokines and inhibiting proliferation of various cancerous cells. The one or more fractions obtained from *Solanum xanthocarpum* that predominantly contain solasodine are effective in one or more of, but are not limited to, inhibiting growth of one or more micro-organism in mammals, inhibiting one or more pro-inflammatory cytokines and inhibiting proliferation of various cancerous cells.

The one or more diseases in which the one or more fractions obtained in accordance with the invention may be effective may include, for example, but are not limited to, Cancer, Arthritis, Ankylosing Spondylitis, Psoriasis, Rheumatoid Arthritis, Osteoarthritis, Multiple sclerosis, Atherosclerosis and Alzheimer's Disease. It should be understood that the method of the invention may be applied to a wide range of plants containing pharmacologically active ingredients. The one or more fractions obtained may therefore be effective in treatment of one or more particular diseases in which the plant material used in the method is effective.

Further, the method generally yields a hydro-alcoholic fraction and a water insoluble fraction. Accordingly, the hydro-alcoholic fraction may be effective in one or more diseases that are different from the one or more diseases in which the water-insoluble fraction is effective. For example, the hydro-alcoholic fraction obtained from *Andrographis paniculata* may be effective in inhibiting one or more pro-inflammatory cytokines Whereas, the water-insoluble fraction obtained from *Andrographis paniculata* may be effective in inhibiting proliferation of various cancerous cells.

In addition, as the method includes one or more of de-pigmentation, de-fatting and detoxifying steps, the one or more fractions obtained in accordance with the various embodiments of the invention contain lesser amount of toxins, fats and pigments that otherwise may impart toxicity to the one or more fractions. Thus, the one or more fractions obtained in accordance with the invention are less toxic in mammals as compared to one or more fractions obtained by conventional methods. For example, the LD 50 value (in mammals like mice) of the one or more fractions obtained from *Andrographis paniculata* that predominantly contain andrographolide may be higher as compared with the LD 50 value of pure andrographolide or an andrographolide extract obtained by conventional methods.

Example 1

Matured stems of the plant *Andrographis paniculata* were obtained from local herb supplier in Pune (India). Methanol, Chloroform and Hexane were of reagent grade and obtained from Merck (India). Water used was in-house distilled water. The matured stems of *Andrographis paniculata* were sun dried and then coarsely powdered. The coarse powder of the matured leaves of *Andrographis paniculata* (500 g) was allowed to soak in a mixture of 5 L of chloroform, 1.5 L of 60% methanol for 8 hours to 12 hours. The mixture was intermittently stirred. After 8 hours to 12 hours the mixture was filtered to obtain the first residue and the first filtrate.

The first filtrate was allowed to settle. The first filtrate once settled had two immiscible layers. The two immiscible layers included an aqueous methanol layer and a chloroform layer. The chloroform layer was separated out. Thereafter, the chloroform layer was concentrated on a rotary evaporator under reduced pressure and dried at 50° C. to obtain a first dry extract. The first dry extract thus obtained was then dissolved in hexane (1 L). The resultant solution was filtered to obtain the second residue and the second filtrate. The second residue was then dried at 50° C. and stored as a first fraction. The first residue obtained as a result of filtering the mixture was then subjected to re-extraction by repeating the steps mentioned above to obtain a second fraction. The first fraction and the second fraction were mixed and stored as AP fraction.

The AP fraction was then used for various studies to determine concentration of various constituents present in the AP fraction, therapeutic effectiveness of the AP fraction in various cancers using animal studies, in-vivo and in-vitro studies, as disclosed in the examples below.

Example 2

Matured leaves of the plant *Solanum xanthocarpum* were obtained from local herb supplier in Pune (India). Methanol, Chloroform and Hexane were of reagent grade and obtained from Merck (India). Water used was in-house distilled water. The matured leaves of *Solanum xanthocarpum* were sun dried and then coarsely powdered. The coarse powder of the matured leaves of *Solanum xanthocarpum* (500 g) was allowed to soak in a mixture 5 L of chloroform, 1.5 L of 60% methanol for 8 hours to 12 hours. The mixture was intermittently stirred. After 8 hours to 12 hours, the mixture was filtered to obtain the first residue and the first filtrate.

The first filtrate was allowed to settle. The first filtrate once settled included two immiscible layers. The two immiscible layers included an aqueous methanol layer and a chloroform layer. The chloroform layer was separated. Thereafter, the chloroform layer was concentrated on a rotary evaporator under reduced pressure and dried at 50° C. to obtain a first dry extract. The first dry extract was then dissolved in hexane (1 L). The resultant solution was filtered to obtain the second residue and the second filtrate. The second residue was then dried at 50° C. and stored as a first fraction. The first residue obtained as a result of filtering the mixture was then subjected to re-extraction by repeating the steps mentioned above to obtain a second fraction. The first fraction and the second fraction were mixed and stored as SX fraction.

The SX fraction was then used for various studies to determine concentration of various constituents present in the fraction, therapeutic effectiveness of the SX fraction in various cancers using animal studies, in-vivo and in-vitro studies, as disclosed in the examples below.

Example 3

The powder of dried stems of *Andrographis paniculata* was extracted using two methods, namely Method 1 and Method 2. For both the methods, the dried stems of *Andrographis paniculata* were obtained from local herbs supplier in Pune (India) and Methanol (reagent grade) was obtained from Merck (India). For Method 2, chloroform and hexane used were of reagent grade and were obtained from Merck (India). The water used in both the methods was in-house distilled water.

Method 1:

The coarse powder (500 g) of the dried stems of *Andrographis paniculata* was transferred to a 5 L flask. 4 L of methanol was added to the flask. The resultant mixture was stirred thoroughly and kept overnight (8 hours to 12 hours). The next day, the mixture was filtered to separate methanol-soluble fraction. The methanol-soluble fraction was then concentrated on a rotary evaporator under reduced pressure and dried at 50° C. to obtain the final extract i.e. the methanol-soluble extract.

Figure 1:
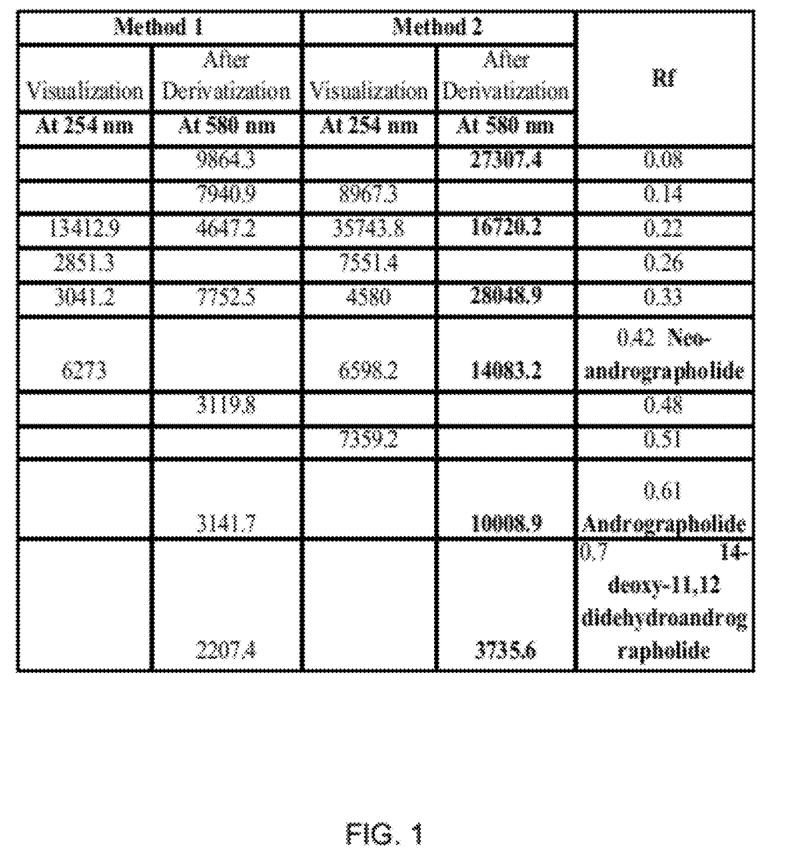
FIG. 1 illustrates a table depicting $R_f$ values for the fractions obtained from *Andrographis paniculata* by using Method 1 and Method 2 in accordance with Example 3.

Method 2:

The coarse powder of the dried stems of *Andrographis paniculata* was extracted using the method as disclosed in Example 1. HPTLC fingerprinting of the fractions obtained by using Method 1 and Method 2 was done. Toluene and ethyl acetate in a concentration ratio of 93:7 were used as mobile phase. Anisaldehyde was used as spraying agent and scanning was done at 580 nm. The $R_f$ values for the fractions obtained by using Method 1 and Method 2 were recorded. FIG. 1 illustrates a table depicting $R_f$ values for the fractions obtained from *Andrographis paniculata* by using Method 1 and Method 2.

It was concluded that concentrations of pharmacologically active ingredients (especially, andrographolide) in the fractions obtained by Method 2 were 30% to 50% greater than the fractions obtained by Method 1.

Example 4

The coarse powder of dried leaves of *Ocimum sanctum* was extracted using two methods, namely Method 1 and Method 2. For both the methods, the dried leaves of *Ocimum sanctum* were obtained from local herbs supplier in Pune (India), and Methanol (reagent grade) was obtained from Merck (India). For Method 2, Chloroform and Hexane used were of reagent grade and obtained from Merck (India). Water used was in-house distilled water.

Method 1:

The coarse powder of the dried leaves of *Ocimum sanctum* was extracted with methanol. The coarse powder (500 g) of dried leaves of *Ocimum sanctum* was transferred to a 5 L flask. 4 L of methanol was added to the flask. The resultant mixture was stirred thoroughly and kept overnight (8 hours to 12 hours). The next day, the mixture was filtered to separate methanol-soluble fraction. The methanol-soluble fraction was then concentrated on a rotary evaporator under reduced pressure and dried at 50° C. to obtain the final extract i.e. the methanol-soluble extract.

Figure 2:
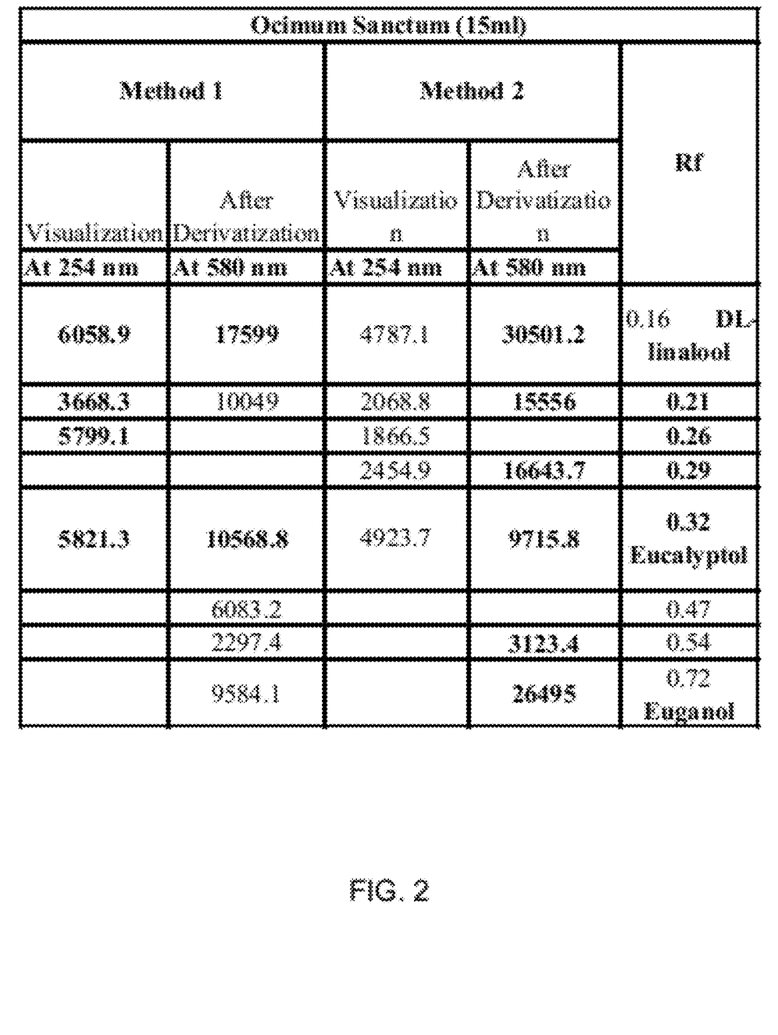
FIG. 2 illustrates a table depicting $R_f$ values for the fractions obtained from *Ocimum sanctum* by using Method 1 and Method 2 in accordance with Example 4.

Method 2:

The coarse powder of the dried leaves of *Ocimum sanctum* was extracted using the method as disclosed in Example 1. HPTLC fingerprinting of the fractions obtained by using Method 1 and Method 2 was done. Toluene and ethyl acetate in a concentration ratio of 93:7 were used as mobile phase. Anisaldehyde was used as spraying agent and scanning was done at 580 nm. The $R_f$ values for the fractions obtained by using Method 1 and Method 2 were recorded. FIG. 2 illustrates a table depicting $R_f$ values for the fractions obtained from *Ocimum sanctum* by using Method 1 and Method 2.

It was concluded that concentrations of pharmacologically active ingredients in the fractions obtained by Method 2 were 15% to 50% greater than the fractions obtained by Method 1.

Example 5

The coarse powder of dried fruits of *Solanum xanthocarpum* was extracted using two methods, namely Method 1 and Method 2. For both the methods, the dried fruits of *Solanum xanthocarpum* were obtained from local herbs supplier in Pune (India) and Methanol (reagent grade) was obtained from Merck (India). For Method 2, chloroform and hexane used were of reagent grade and were obtained from Merck Laboratory (India). The water used in both the methods was in-house distilled water.

Method 1:

The coarse powder of the dried fruits of *Solanum xanthocarpum* was transferred to a 5 L flask. 4 L of methanol was added to the flask. The resultant mixture was stirred thoroughly and kept overnight (8 hours to 12 hours). The next day, the mixture was filtered to separate methanol-soluble fraction. The methanol-soluble fraction was then concentrated on a rotary evaporator under reduced pressure and dried at 50° C. to obtain the final extract i.e. the methanol-soluble extract.

Figure 3:
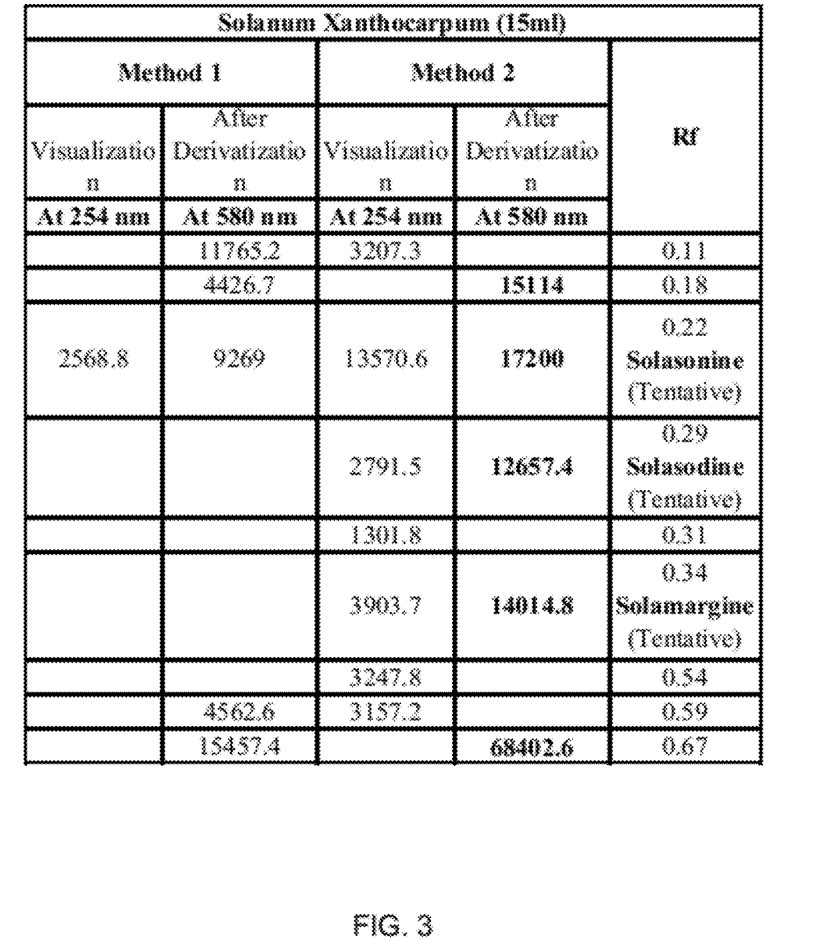
FIG. 3 illustrates a table depicting $R_f$ values for the fractions obtained from *Solanum xanthocarpum* by using Method 1 and Method 2 in accordance with Example 5.

Method 2:

The powder of the dried fruits of *Solanum xanthocarpum* was extracted using the method as disclosed in Example 1. HPTLC fingerprinting of the fractions obtained by using Method 1 and Method 2 was done. Toluene and ethyl acetate in a concentration ratio of 93:7 were used as mobile phase. Anisaldehyde was used as spraying agent and scanning was done at 580 nm. The $R_f$ values for the fractions obtained by using Method 1 and Method 2 were recorded. FIG. 3 illustrates a table depicting $R_f$ values for the fractions obtained from *Solanum xanthocarpum* by using Method 1 and Method 2.

It was concluded that concentrations of pharmacologically active ingredients in the fractions obtained by Method 2 were 50% to 70% greater than the fractions obtained by Method 1.

Example 6

Anti-Inflammatory Activity of the AP Fraction

Edema represents an early phase of inflammation characterized by an initial release of histamine and 5-hydroxytryptamine (5-HT) producing an early vascular permeability followed by release of cytokines, further contributing to increased vascular permeability. Lastly, the prostaglandins and slow releasing substances (SRS) are released to maintain the increased vascular permeability produced by histamine, 5-HT and cytokines. This model was used for studying anti-inflammatory activity of the AP fraction.

Six rats per group (hereinafter, "animals") were selected for carrageenan-induced rat paw edema model to study anti-inflammatory effect of the AP fraction. The AP fraction (hereinafter "AP Extract 2") was obtained in accordance with Method 2 of Example 4 (BIO-VED Pharmaceuticals Pvt. Ltd., B. No.: APD120510, Expiry date: 2012). The fractions (hereinafter, "AP Extract 1") obtained in accordance with Method 1 of Example 4 (BIO-VED Pharmaceuticals Pvt. Ltd., B. No.: APM120510, Expiry date: 2012) were also studied for their anti-inflammatory effect. Carrageenan was obtained from Ottokemi, with B. No. C 1675. Diclofenac sodium was obtained from Novartis (India) with B. No. 82014V and Expiry date January 2011.

0.1 ml Carrageenan solution (1% W/V) was injected transdermally in the right paws of each animal to produce swelling which was measured by a Plethysmograph. Whereas, left paws were kept as control. A comparative study of extent of rat paw swelling in control group, group given Diclofenac sodium (15 mg/kg body weight), group given the AP Extract 1 (100 mg/kg body weight), and group given the AP Extract 2 (100 mg/kg body weight) were conducted and results recorded.

Figure 4:
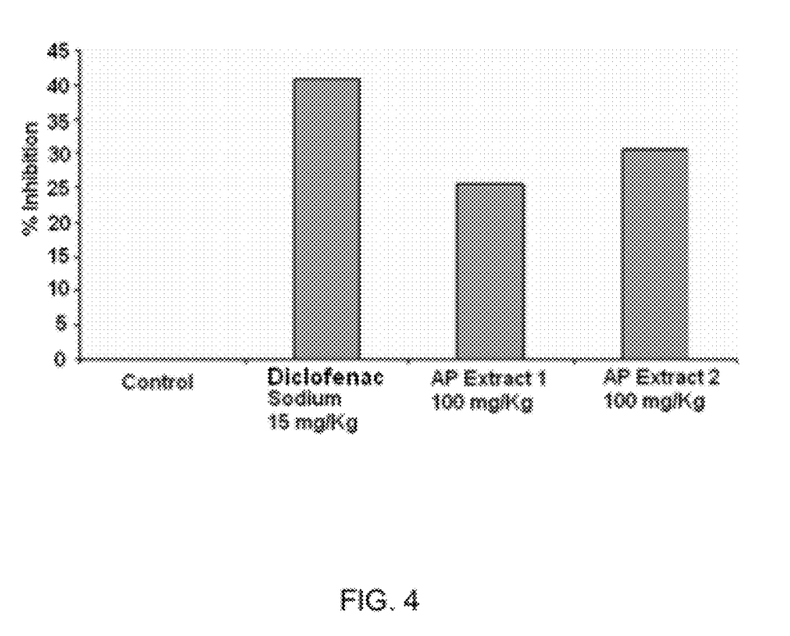
FIG. 4 illustrates a graph illustrating percent inhibition of carrageenan-induced rat paw edema using Diclofenac sodium, the AP Extract 1 and the AP Extract 2 in accordance with Example 6.

FIG. 4 illustrates a graph illustrating percent inhibition of carrageenan-induced rat paw edema using Diclofenac sodium, the AP Extract 1 and the AP Extract 2. It was concluded that the percent inhibition of carrageenan-induced rat paw edema using the AP Extract 2 was comparable with that using Diclofenac sodium. Further, the percent inhibition of carrageenan-induced rat paw edema using the AP Extract 2 was greater as compared with the percent inhibition of carrageenan-induced rat paw edema using the AP Extract 1 (conventional method).

Example 7

Anti-Inflammatory Activity of the SX Fraction and the Os Fraction

Six rats per group (hereinafter, "animals") were selected for carrageenan-induced rat paw edema model to study anti-inflammatory effect of the *Solanum xanthocarpum* fraction i.e. the SX fraction (hereinafter, "SX Extract 2") and *Ocimum sanctum* fraction (hereinafter, "OS Extract 2"). The SX Extract 2 was obtained in accordance with Method 2 of Example 4 (BIO-VED Pharmaceuticals Pvt. Ltd., B. No.: SXD130510, Expiry date: 2012), OS Extract 2 was obtained in accordance with Method of Example 1 (BIO-VED Pharmaceuticals Pvt. Ltd., B. No.: OSD130510, Expiry date: 2012). The fractions obtained in accordance with Method 1 of Example 4 i.e. SX Extract 1 (BIO-VED Pharmaceuticals Pvt. Ltd., B. No.: SXM130510, Expiry date: 2012) and OS Extract 1 (BIO-VED Pharmaceuticals Pvt. Ltd., B. No.: OSM130510, Expiry date: 2012) were also studied for their anti-inflammatory effect. Carrageenan was obtained from Ottokemi, with B. No. C 1675. Diclofenac sodium was obtained from Novartis (India) with B. No. 82014V and Expiry date January 2011.

In this study, the SX Extract 2 and the OS Extract 2 represented the fractions obtained in accordance with the invention whereas the SX Extract 1 and the OS Extract 1 represented the fractions obtained by conventional methods. 0.1 ml Carrageenan solution (1% W/V) was injected transdermally in the right paws of each animal to produce swelling which was measured by a Plethysmograph. Whereas, left paws were kept as control. A comparative study of extent of rat paw swelling in control group, group given Diclofenac sodium (15 mg/kg body weight), group given the SX Extract 1 (100 mg/kg body weight), group given the SX Extract 2 (100 mg/kg body weight), group given the OS Extract 1 (100 mg/kg body weight), and group given the OS Extract 2 (100 mg/kg body weight) were conducted and results recorded.

Figure 5:
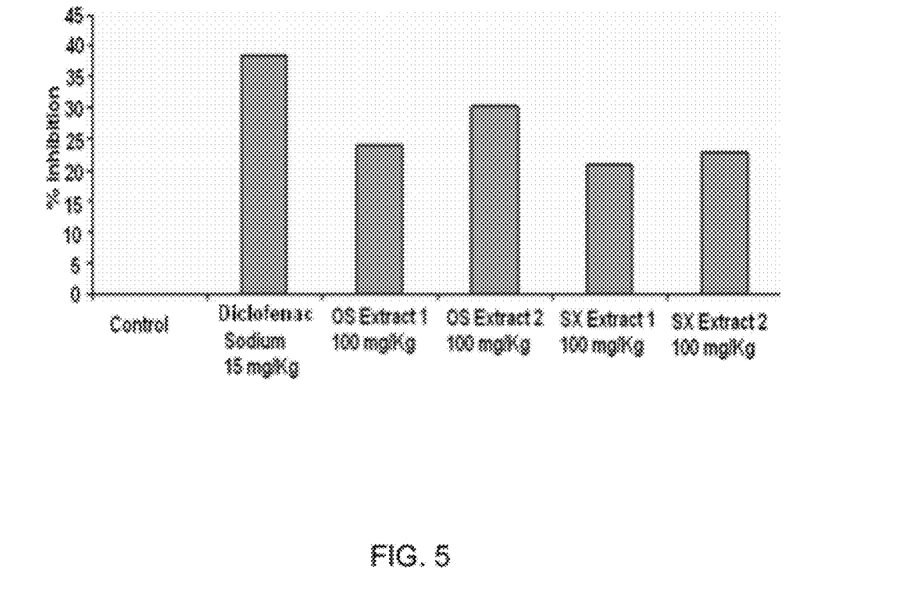
FIG. 5 illustrates a graph illustrating percent inhibition of carrageenan-induced rat paw edema using Diclofenac sodium, the SX Extract 1, the SX Extract 2, the OS Extract 1 and the OS Extract 2 in accordance with Example 7.

FIG. 5 illustrates a graph illustrating percent inhibition of carrageenan-induced rat paw edema using Diclofenac sodium, the SX Extract 1, the SX Extract 2, the OS Extract 1 and the OS Extract 2. It was concluded that the percent inhibition of carrageenan-induced rat paw edema using the SX Extract 2 and OS Extract 2 was comparable with that using Diclofenac sodium. Further, the percent inhibition of carrageenan-induced rat paw edema using the SX Extract 2 was greater as compared with the percent inhibition of carrageenan-induced rat paw edema using the SX Extract 1 (conventional method). Also, the percent inhibition of carrageenan-induced rat paw edema using the OS Extract 2 was greater as compared with the percent inhibition of carrageenan-induced rat paw edema using the OS Extract 1.

Example 8

Anti-Microbial Activity of the AP Extract 2, SX Extract 2 and OS Extract 2

The AP Extract 2, SX Extract 2, OS Extract 2, AP Extract 1, SX Extract 1 and OS Extract 1 were obtained as illustrated in Example 6 and 7, above. In this study AP Extract 1, SX Extract 1 and OS Extract 1 represented the fractions obtained according to conventional methods whereas AP Extract 2, SX Extract 2 and OS Extract 2 represented the fractions obtained in accordance with the invention.

*Pseudomonas aeruginosa* (ATCC 9027) strain was used as test organisms. The culture media, Nutrient Agar (NA), Nutrient Broth (NB) and Czapek Yeast Extract Agar (CYA) used for the growth of microorganisms, were purchased from Hi-Media. All other chemicals, including organic solvents used for the extraction of the plant metabolites, were of analytical grade.

The AP Extract 2, SX Extract 2, OS Extract 2, AP Extract 1, SX Extract 1 and OS Extract 1 were separately dissolved in 100% aqueous dimethylsulfoxide (DMSO) to obtain a final concentration of 100 mg/ml for each extract. 100 mg/ml solution of Chloramphenicol was prepared and used as a Positive control. Antimicrobial activity of the above mentioned extracts was determined, using the agar well diffusion assay method (Perez et al., 1990). Approximately 20 ml of molten and cooled media (NA and CYA) were poured in sterilized Petri dishes. The plates were left overnight at room temperature to check for any contamination to appear. The test organism was grown in nutrient broth for 24 hours. A 100 μl nutrient broth culture of each bacterial organism was used to prepare bacterial lawns.

Agar wells of 5 mm diameter were prepared with the help of a sterilized stainless steel cork borer. Five wells (four on the periphery and one in the center) were prepared in the agar plates. The wells in each plate were loaded with 100 μl of the various extracts, separately. The central well in each plate was used as a control and loaded with 100 μl of solvent or sterilized distilled water, as the case may be. The plates containing the test animals and the extracts were incubated at 37° C. The antimicrobial activity of the extracts was taken on the basis of diameter of zone of inhibition, which was measured at cross-angles after 24 hours of incubation and the mean of three readings for each extract.

The zones of inhibition for SX Extract 1, SX Extract 2, OS Extract 1, OS Extract 2, AP Extract 1 and AP Extract 2 were found to be 0 mm, 24.75 mm, 20 mm, 14 mm, 21 mm, 25 mm, respectively. Whereas, zone of inhibition for the positive standard was found to be 40 mm. Based on these findings, it was concluded that SX Extract 1 (obtained by conventional method) does not have antimicrobial activity whereas the SX Extract 2 (obtained in accordance with the invention) has significant anti-microbial activity. Further, it was concluded that the AP Extract 2 had greater anti-microbial activity as compared to AP Extract 1 (obtained by conventional method).

Various embodiments of the invention provide a method for extraction one or more fractions from one or more plants. The one or more fractions obtained in accordance with the various embodiments of the invention contain a desired pharmacologically active ingredient in a concentration predominantly greater than concentrations of other pharmacologically active ingredients present in the one or more fractions. Further, the one or more fractions obtained in accordance with the various embodiments of the invention are less toxic in mammals as compared to corresponding one or more extracts obtained by conventional methods of extraction. In addition, the one or more fractions are therapeutically more effective as compared to one or more fractions obtained by conventional methods of extraction.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made to the invention without departing from the scope of the invention. Accordingly, the specification is to be regarded in an illustrative rather than a restrictive sense, and all such modifications are intended to be included within the scope of the invention.

What is claimed is:

1. A method of extracting a pharmacologically active fraction from *Andrographis paniculata* stems, wherein the pharmacologically active fraction includes concentrations of pharmacologically active ingredients, and wherein one of the pharmacologically active ingredients is andrographolide, comprising:

soaking stems of *Andrographis paniculata* in chloroform and aqueous 60% methanol for 8-12 hours;

filtering the chloroform and aqueous 60% methanol to obtain a first residue and a first filtrate;

settling the first filtrate to provide two immiscible layers, wherein the two immiscible layers are an aqueous methanol layer and a chloroform layer;

separating the chloroform layer;

concentrating the chloroform layer to obtain a first dry extract;

dissolving the first dry extract in hexane;

filtering the first dry extract dissolved in hexane to obtain a second residue and second filtrate;

drying the second residue and storing as a first fraction;

re-extracting the first fraction to obtain a second fraction; and combining the first and second fractions to provide the pharmacologically active fraction;

wherein said pharmacologically active fraction treats inflammation.

2. The method of claim 1, further comprising one of performing a de-pigmentation step, performing a de-fatting step, and performing a detoxification step to decrease a toxicity level of the pharmacologically active fraction.

3. The method of claim 2, wherein one of the de-pigmentation step, the de-fatting step, and the detoxification step is performed with an agent selected from the group consisting of pentane, hexane, heptanes, diethyl ether, petroleum ether, ethylene chloride, methylene chloride, cyclohexane and solvent ether.

* * * * *